US00PP18927P2

(12) United States Plant Patent
Smith

(10) Patent No.: US PP18,927 P2
(45) Date of Patent: Jun. 10, 2008

(54) ***CHRYSANTHEMUM* PLANT NAMED 'YOJACQUELINE'**

(50) Latin Name: *Chrysanthemum×morifolium*
Varietal Denomination: Yojacqueline

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 11/641,399

(22) Filed: Dec. 18, 2006

(51) Int. Cl.
*A01H 5/00* (2006.01)

(52) U.S. Cl. ..... Plt./287

(58) Field of Classification Search ..... Plt./287
See application file for complete search history.

*Primary Examiner*—Anne Marie Grunberg
*Assistant Examiner*—S. B. McCormick-Ewoldt
(74) *Attorney, Agent, or Firm*—C. A. Whealy

(57) ABSTRACT

A new and distinct cultivar of *Chrysanthemum* plant named 'Yojacqueline', characterized by its compact, upright and outwardly spreading plant habit; freely branching habit; dense and full plant habit; uniform and freely flowering habit; decorative-type inflorescences with elongated oblong to ligulate-shaped ray florets; light lavender and lavender-colored ray florets; and natural season flowering about September 25$^{th}$ in the Northern Hemisphere.

1 Drawing Sheet

Botanical designation: *Chrysanthemum×morifolium.*
Cultivar denomination: 'Yojacqueline'.

BACKGROUND OF THE INVENTION

The present invention relates to a new and distinct cultivar of *Chrysanthemum* plant, botanically known as *Chrysanthemum×morifolium,* commercially grown as a garden *Chrysanthemum* and hereinafter referred to by the name 'Yojacqueline'.

The objective of the breeding program is to create new garden-type *Chrysanthemum* cultivars having inflorescences with desirable inflorescence forms, attractive floret colors and good garden performance.

The new *Chrysanthemum* originated from a cross-pollination made by the Inventor in February, 2003, in Salinas, Calif. of the *Chrysanthemum×morifolium* cultivar Gedi One Sav, disclosed in U.S. Plant Pat. No. 13,928, as the female, or seed, parent with the *Chrysanthemum×morifolium* cultivar Yoursula, disclosed in U.S. Plant Pat. No. 13,641, as the male, or pollen, parent. The new *Chrysanthemum* was discovered and selected by the Inventor as a single flowering plant within the progeny of the stated cross-pollination in a controlled environment in Alva, Fla. in October, 2003.

Asexual reproduction of the new *Chrysanthemum* by vegetative cuttings was first conducted in Alva, Fla. in December, 2003. Asexual reproduction by cuttings has shown that the unique features of this new *Chrysanthemum* are stable and reproduced true to type in successive generations.

SUMMARY OF THE INVENTION

Plants of the cultivar Yojacqueline have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yojacqueline'. These characteristics in combination distinguish 'Yojacqueline' as a new and distinct garden *Chrysanthemum* cultivar:

1. Compact, upright and outwardly spreading plant habit.
2. Freely branching habit; dense and full plant habit.
3. Uniform and freely flowering habit.
4. Decorative-type inflorescences with elongated oblong to ligulate-shaped ray florets.
5. Light lavender and lavender-colored ray florets.
6. Natural season flowering about September 25$^{th}$ in the Northern Hemisphere.

In side-by-side comparisons conducted in Alva, Fla., plants of the new *Chrysanthemum* differed from plants of the female parent, the cultivar Gedi One Sav, in the following characteristics:

1. Plants of the new *Chrysanthemum* were smaller than plants of the cultivar Gedi One Sav.
2. Plants of the new *Chrysanthemum* flowered earlier than plants of the cultivar Gedi One Sav when grown under natural season conditions.
3. Ray florets of plants of the new *Chrysanthemum* were light lavender and lavender in color whereas ray florets of plants of the cultivar Gedi One Sav were greyed purple in color.
4. Ray florets of plants of the new *Chrysanthemum* retained color longer than ray florets of plants of the cultivar Gedi One Sav.

In side-by-side comparisons conducted in Alva, Fla. plants of the new *Chrysanthemum* differed from plants of the male parent, the cultivar Yoursula, in the following characteristics:

1. Plants of the new *Chrysanthemum* were larger than plants of the cultivar Yoursula.
2. Plants of the new *Chrysanthemum* had larger inflorescences than plants of the cultivar Yoursula.

2. Plants of the new *Chrysanthemum* had larger inflorescences than plants of the cultivar Yoursula.
3. Plants of the new *Chrysanthemum* and the cultivar Yoursula differed in ray floret coloration as plants of the cultivar Yoursula had light purple-colored ray florets.

Plants of the new *Chrysanthemum* can be compared to plants of the *Chrysanthemum* cultivar Debonair, disclosed in U.S. Plant Pat. No. 5,324. In side-by-side comparisons conducted in Alva, Fla., plants of the new *Chrysanthemum* differed from plants of the cultivar Debonair in the following characteristics:

1. Plants of the new *Chrysanthemum* were larger and more mounded than plants of the cultivar Debonair.
2. Plants of the new *Chrysanthemum* flowered more uniformly than plants of the cultivar Debonair.
3. Plants of the new *Chrysanthemum* had smaller inflorescences than plants of the cultivar Debonair.
4. Plants of the new *Chrysanthemum* and the cultivar Debonair differed in ray floret coloration.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph at the bottom of the sheet comprises a side perspective view of a typical flowering plant of 'Yojacqueline'.

The photograph at the top of the sheet is a close-up view of typical inflorescences of 'Yojacqueline'.

DETAILED BOTANICAL DESCRIPTION

The aforementioned photographs and following observations and measurements describe plants grown in Pendleton, S.C. during the summer in an outdoor nursery and under conditions and practices which approximate those generally used in commercial garden *Chrysanthemum* production. During the production of the plants, day temperatures averaged 32° C. and night temperatures averaged 21° C. Plants were grown in 15-containers and exposed to long day/short night conditions for about three weeks, then exposed to natural season photoinductive conditions. Plants used in the photographs and for the description were about three months old. In the following description, color references are made to The Royal Horticultural Society Colour Chart, 1995 Edition, except where general terms of ordinary dictionary significance are used.

Botanical classification: *Chrysanthemum×morifolium* cultivar Yojacqueline.

Parentage:

*Female, or seed, parent.*—*Chrysanthemum×morifolium* cultivar Gedi One Sav, disclosed in U.S. Plant Pat. No. 13,928.

*Male, or pollen, parent.*—*Chrysanthemum×morifolium* cultivar Yoursula, disclosed in U.S. Plant Pat. No. 13,641.

Propagation:

*Type.*—Terminal vegetative cuttings.

*Time to initiate roots.*—About four days at temperatures of about 21° C.

*Time to produce a rooted young plant.*—About ten to twelve days at temperatures of about 21° C.

*Root description.*—Fine, fibrous; white in color.

*Rooting habit.*—Freely branching.

Plant description:

*Appearance.*—Herbaceous decorative-type garden *Chrysanthemum*. Stems upright and outwardly spreading giving a uniformly mounded appearance to the plant. Freely branching habit, about six lateral branches develop after removal of terminal apex (pinching) each with numerous secondary laterals; dense and full plant habit. Strong and vigorous growth habit.

*Plant height.*—About 22 cm.

*Plant width.*—About 39 cm.

*Lateral branches.*—Length: About 22 cm. Diameter: About 1.3 cm. Internode length: About 1.9 cm. Strength: Strong. Texture: Pubescent. Color: 146A.

*Leaves.*—Arrangement: Alternate, simple. Length: About 3.1 cm. Width: About 2.6 cm. Apex: Acute to cuspidate. Base: Obtuse. Margin: Palmately lobed, sinuses between lateral lobes parallel to divergent. Texture, upper and lower surfaces: Fine pubescence; veins prominent on lower surface. Color: Developing foliage, upper and lower surfaces: 147A. Fully expanded foliage, upper surface: 147A; venation, 147C. Fully expanded foliage, lower surface: 147B; venation, 147C. Petiole: Length: About 1 cm. Diameter: About 2 mm. Texture, upper and lower surfaces: Pubescent. Color, upper surface: 147A to 147B. Color, lower surface: 147B.

Inflorescence description:

*Appearance.*—Decorative-type inflorescence form with elongated oblong to ligulate-shaped ray florets. Inflorescences borne on terminals above foliage. Disk and ray florets arranged acropetally on a capitulum. Inflorescences not fragrant.

*Flowering response.*—Early flowering habit; under natural season conditions, plants flower about September 25$^{th}$ in the Northern Hemisphere. At other times of the year, inflorescence initiation and development can be induced under short day/long night conditions (at least 13.5 hours of darkness).

*Postproduction longevity.*—Inflorescences maintain good color and substance for about four weeks in an outdoor nursery.

*Quantity of inflorescences.*—About 35 to 36 inflorescences develop per lateral branch.

*Inflorescence bud.*—Height: About 1.2 cm. Diameter: About 1 cm. Shape: Oblate. Color: 76C.

*Inflorescence size.*—Diameter: About 3.6 cm. Depth (height): About 1.4 cm. Receptacle diameter: About 1.5 cm. Receptacle height: About 4 mm.

*Ray florets.*—Shape: Elongated-oblong to ligulate. Orientation: Initially upright, then about 90° from vertical or perpendicular to peduncle. Aspect: Initially incurved, then mostly concave. Length: About 2 cm. Width: About 6 mm. Apex: Emarginate to rounded. Base: Acute. Margin: Entire. Texture, upper and lower surfaces: Smooth, glabrous, satiny. Number of ray florets per inflorescence: About 160 arranged in about 14 to 15 whorls. Color: When opening, upper surface: Towards the apex, 75B; towards the base, 75C to 75D. When opening, lower surface: Towards the apex, 76C; towards the base, 155D. Fully opened, upper surface: Towards the apex, 77B; midsection, 77C; towards the base, 77D. With development, apices become closer to 78A in color. Fully opened, lower surface: Towards the apex, 75B; towards the base, 76D. With development, color becomes closer to 78A to 78C.

*Disc florets.*—None observed.

*Phyllaries.*—Number of phyllaries per inflorescence: About 40 arranged in about three whorls. Length: About 6 mm. Width: About 3 mm. Shape: Elliptic. Apex: Acute. Base: Truncate. Texture, upper surface: Smooth, waxy. Texture, lower surface: Pubescent. Color, upper surface: Close to 144A. Color, lower surface: Close to 146B.

*Peduncles.*—Length: About 5 cm. Diameter: About 2 mm. Angle: About 50° to 70° from vertical. Strength: Strong. Texture: Pubescent; longitudinally ridged. Color: Close to 147B.

*Reproductive organs.*—Androecium: None observed. Gynoecium: Pistil length: About 6 mm. Stigma shape: Bi-parted. Stigma color: Close to 145D. Style length: About 3 mm. Style color: Close to 145D. Ovary color: Close to 145B.

*Seed/fruit.*—Seed and fruit production has not been observed.

Disease/pest resistance: Resistance to pathogens and pests common to *Chrysanthemums* has not been observed on plants grown under commercial conditions.

Garden performance: Plants of the new *Chrysanthemum* have demonstrated excellent garden performance and to tolerate temperatures from about 0° C. to about 38° C.

It is claimed:

1. A new and distinct *Chrysanthemum* plant named 'Yojacqueline' as illustrated and described.

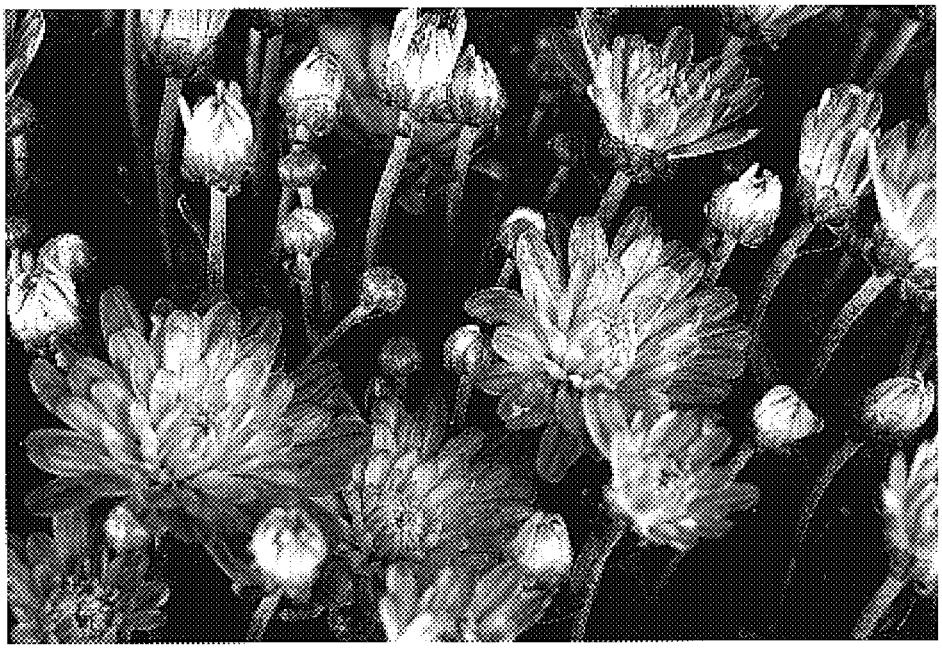
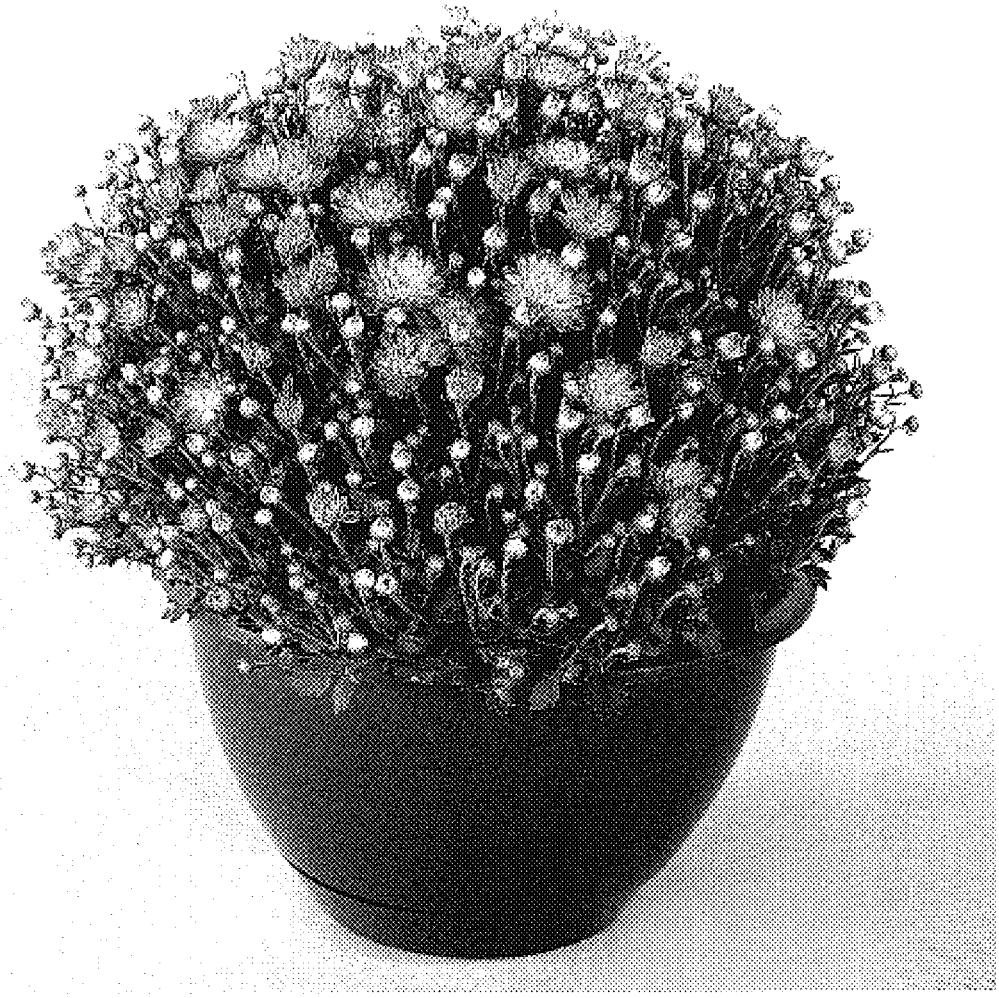

* * * * *